United States Patent [19]

Verma et al.

[11] Patent Number: 5,470,736
[45] Date of Patent: Nov. 28, 1995

[54] TRANSDOMINANT NEGATIVE PROTO-ONCOGENE

[75] Inventors: Inder M. Verma, Solana Beach; Ronald M. Wisdom, Del Mar, both of Calif.; Jong-Young J. Yen, West Orange, N.J.

[73] Assignee: The Salk Institute for Biological Studies, La Jolla, Calif.

[21] Appl. No.: 218,686

[22] Filed: Mar. 28, 1994

Related U.S. Application Data

[63] Continuation of Ser. No. 710,862, Jun. 10, 1991, abandoned.

[51] Int. Cl.[6] .............................. C12N 15/12; C12N 5/10; C12N 15/79; C12N 15/86
[52] U.S. Cl. .................. 435/240.2; 435/69.1; 435/172.3; 435/252.3; 435/320.1; 536/23.1; 536/23.5; 536/24.5; 935/11; 935/27; 935/32; 935/36; 935/54; 935/57; 935/62; 935/66
[58] Field of Search .............................. 435/69.1, 172.3, 435/240.2, 252.3, 320.1; 536/23.1, 23.5, 24.5; 935/11, 27, 32, 36, 54, 57, 62, 66

[56] References Cited

U.S. PATENT DOCUMENTS

| | | | |
|---|---|---|---|
| 4,738,922 | 4/1988 | Haseltine et al. | 435/69.3 |
| 4,833,080 | 5/1989 | Brent et al. | 435/172.3 |
| 4,981,790 | 1/1991 | Haseltine et al. | 435/69.1 |
| 5,004,810 | 4/1991 | Draper | 536/24.5 |

OTHER PUBLICATIONS

P. Roux et al. Proc. Natl. Acad. Sci. 86:9079–9083 (Dec. 1989).
M. Mizuno et al. Cancer Res. 50:7826–7829 (Dec. 1990).
P. Sassone–Corsi et al. Nature 336:692–695 (Dec. 1988).
Lynn J. Ransone, et al.; Nuclear Proto–Oncogenes Fos and Jun; Annu. Rev. Cell Biol. 1990 6:539–57.
William W. Lamph, et al.; Negative and positive regulation by transcription . . . ; Proc. Natl. Acad. Sci. USA, vol. 87, 4320–4324 (1990).
Dirk Bohmann, et al.; Human Proto–Oncogene c–jun Encodes a DNA Binding Protein . . . ; Science, vol. 238, Dec. 1987, 1386–1392.
Marino zerial, et al; The product of a novel growth factor activated gene . . . ; The EMBO Journal, vol. 8 no. 3, 805–813, 1989.
Paolo Sassone–Corsi, et al., fos–Associated Cellular p39 is Related . . . ; Cell, vol. 54, 553–560, Aug. 12, 1988.
Jochen Schutte, et al.; jun–B Inhibits and c–fos Stimulates the Transforming . . . ; Cell, vol. 59, 987–997, Dec. 22, 1989.
Nakabeppu, Y. et al. "A Naturally Occurring Truncated Form of Fos B that Inhibits Fos/Jun Transcriptional Activity" Cell 64:751–759 (Feb. 22, 1991).
Noguchi, T. et al. "Genomic Structure of the Fos B Gene: Differential Splicing Gives Rise to Two Transcripts" J. Cell. Biochem. Suppl. 15B:215 (Jan. 1991).
Sassone–Corsi, P. et al. "Direct Interaction between fos and jun . . . " Nature 336:692–695 (Dec. 1988).
Mizuno, M. et al. "Growth Inhibitor of Glioma Cells Transfected with the . . . " Cancer Res. 50:7826–7829 (Dec. 1990).
Roux, P. et al. "A versatile and potentially general approach to the targeting of specific cell types by retroviruses: . . . " Proc. Natl. Acad. Sci.: 86:9079–9083 (Dec. 1989).

*Primary Examiner*—Robert A. Wax
*Assistant Examiner*—Rebecca Prouty
*Attorney, Agent, or Firm*—Fish & Richardson

[57] ABSTRACT

The present invention provides polynucleotide and polypeptide sequences for a trans-repressing protein of the Fos proto-oncogene family, where the polypeptide is characterized by having a leucine zipper domain and forming a heterodimer with a Jun related protein. This heterodimer is capable of biding to an AP-1 site and suppressing transcriptional transactivation of a promoter containing the AP-1 site.

20 Claims, 3 Drawing Sheets

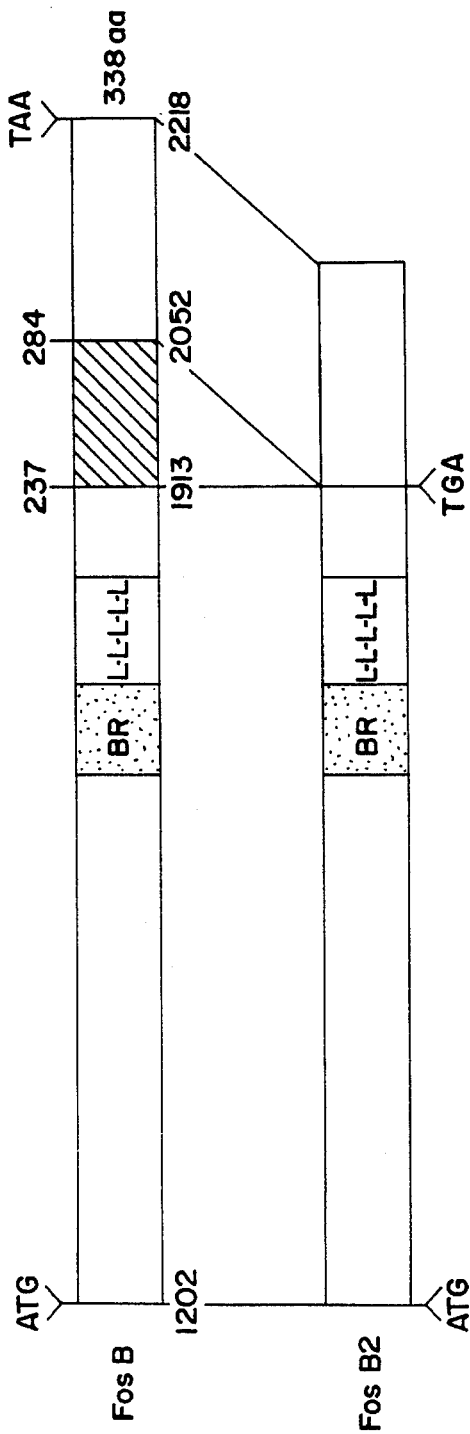

```
                                        ATAAATTCTTATT   13
TTGACACTCACCAAAATAGTCACCTGGAAAACCCGCTTTTTGTGACAAAGTACA   67
GAAGGCTTGGTCACATTTAAATCACTGAGAACTAGAGAGAAATACTATCGCAAA  121
CTGTAATAGACATTACATCCATAAAAGTTTCCCCAGTCCTTATTGTAATATTGC  175
ACAGTGCAATTGCTACATGGCAAACTAGTGTAGCATAGAAGTCAAAGCAAAAAC  229
AAACCAAAGAAAGGAGCCACAAGAGTAAAACTGTTCAACAGTTAATAGTTCAAA  283
CTAAGCCATTGAATCTATCATTGGGATCGTTAAAATGAATCTTCCTACACCTTG  337
CAGTGTATGATTTAACTTTTACAGAACACAAGCCAAGTTTAAAATCAGCAGTAG  391
AGATATTAAAATGAAAAGGTTTGCTAATAGAGTAACATTAAATACCCTGAAGGA  445
AAAAAAACCTAAATATCAAAATAACTGATTAAAATTCACTTGCAAATTAGCACA  499
CGAATATGCAACTTGGAAATCATGCAGTGTTTTATTTAAGAAAACATAAAACAA  553
AACTATTAAAATAGTTTTAGAGGGGGTAAAATCCAGGTCCTCTGCCAGGATGCT  607
AAAATTAGACTTCAGGGGAATTTTGAAGTCTTCAATTTTGAAACCTATTAAAAA  661
GCCCATGATTACAGTTAATTAAGAGCAGTGCACGCAACAGTGACACGCCTTTAG  715
AGAGCATTACTGTGTATGAACATGTTGGCTGCTACCAGCCACAGTCAATTTAAC  769
AAGGCTGCTCAGTCATGAACTTAATACAGAGAGAGCACGCCTAGGCAGCAAGCA  823
CAGCTTGCTGGGCCACTTTCCTCCCTGTCGTGACACAATCAATCCGTGTACTTG  877
GTGTATCTGAAGCGCACGCTGCACCGCGGCACTGCCCGGCGGGTTTCTGGGCGG  931
GGAGCGATCCCCGCGTCGCCCCCGTGAAACCGACAGAGCCTGGACTTTCAGGA   985
GGTACAGCGGCGGTCTGAAGGGGATCTGGGATCTTGCAGAGGGAACTTGCATCG 1039
AAACTTGGGCAGTTCTCCGAACCGGAGACTAAGCTTCCCCGAGCAGCGCACTTT 1093
GGAGACGTGTCCGGTCTACTCCGGACTCGCATCTCATTCCACTCGGCCATAGCC 1147
TTGGCTTCCCGGCGACCTCAGCGTGGTCACAGGGGCCCCCCTGTGCCCAGGGAA 1201

M   F   Q   A   F   P   G   D   Y   D   S   G   S   R   C   S   S   S    18
ATGTTTCAAGCTTTTCCCGGAGACTACGACTCCGGCTCCCGGTGTAGCTCATCA 1255

P   S   A   E   S   Q   Y   L   S   S   V   D   S   F   G   S   P   P    36
CCCTCCGCCGAGTCTCAGTACCTGTCTTCGGTGGACTCCTTCGGCAGTCCACCC 1309

T   A   A   A   S   Q   E   C   A   G   L   G   E   M   P   G   S   F    54
ACCGCCGCCGCCTCCCAGGAGTGCGCCGGTCTCGGGGAAATGCCCGGCTCCTTC 1363

V   P   T   V   T   A   I   T   T   S   Q   D   L   Q   W   L   V   Q    72
GTGCCAACGGTCACCGCAATCACAACCAGCCAGGATCTTCAGTGGCTCGTGCAA 1417

P   T   L   I   S   S   M   A   Q   S   Q   G   Q   P   L   A   S   Q    90
CCCACCCTCATCTCTTCCATGGCCCAGTCCCAGGGGCAGCCACTGGCCTCCCAG 1471

P   P   A   V   D   P   Y   D   M   P   G   T   S   Y   S   T   P   G   108
CCTCCAGCTGTTGACCCTTATGACATGCCAGGAACCAGCTACTCAACCCCAGGC 1525

L   S   A   Y   S   T   G   G   A   S   G   S   G   G   P   S   T   S   126
CTGAGTGCCTACAGCACTGGCGGGGCAAGCGGAAGTGGTGGGCCTTCAACCAGC 1579

T   T   T   S   G   P   V   S   A   R   P   A   R   A   R   P   R   R   144
ACAACCACCAGTGGACCTGTGTCTGCCCGTCCAGCCAGAGCCAGGCCTAGAAGA 1633

P   R   E   E   T   L   T   P   E   E   E   E   K   R   R   V   R   R   162
CCCCGAGAAGAGACACTTACCCCAGAAGAAGAAGAAAAGCGAAGGGTTCGCAGA 1687

E   R   N   K   L   A   A   A   K   C   R   N   R   R   R   E   L   T   180
GAGCGGAACAAGCTGGCTGCAGCTAAGTGCAGGAACCGTCGGAGGGAGCTGACA 1741

D   R   L   Q   A   E   T   D   Q   L   E   E   E   K   A   E   L   E   198
GATCGACTTCAGGCGGAAACTGATCAGCTTGAAGAGGAAAAGGCAGAGCTGGAG 1795

S   E   I   A   E   L   Q   K   E   K   E   R   L   E   F   V   L   V   216
TCGGAGATCGCCGAGCTGCAAAAAGAGAAGGAACGCCTGGAGTTTGTCCTGGTG 1849
```

FIG.2A

```
  A   H   K   P   G   C   K   I   P   Y   E   E   G   P   G   P   G   P    234
GCCCACAAACCGGGCTGCAAGATCCCCTACGAAGAGGGGCCGGGGCCAGGCCCG                     1903

L   A   E   V   R   D   L   P   G   S   T   S   A   K   E   D   G   F    252
CTGGCCGAGGTGAGAGATTTGCCAGGGTCAACATCCGCTAAGGAAGACGGCTTC                     1957

G   W   L   L   P   P   P   P   P   P   P   L   P   F   Q   S   S   R    270
GGCTGGCTGCTGCTGCCCCCTCCACCACCCCCCTGCCCTTCCAGAGCAGCCGA                      2011

D   A   P   P   N   L   T   A   S   L   F   T   H   S   E   V   Q   V    288
GACGCACCCCCCAACCTGACGGCTTCTCTCTTTACACACAGTGAAGTTCAAGTC                     2055

L   G   D   P   F   P   V   V   S   P   S   Y   T   S   S   F   V   L    306
CTCGGCGACCCCTTCCCCGTTGTTAGCCCTTCGTACACTTCCTCGTTTGTCCTC                     2119

T   C   P   E   V   S   A   F   A   G   A   Q   R   T   S   G   S   E    324
ACCTGCCCGGAGGTCTCCGCGTTCGCCGGCGCCCAACGCACCAGCGGCAGCGAG                     2173

Q   P   S   D   P   L   N   S   P   S   L   L   A   L   *                338
CAGCCGTCCGACCCGCTGAACTCGCCCTCCCTTCTTGCTCTGTAAACTCTTTAG                     2227

ACAAACAAAACAAACAAACCCGCAAGGAACAAGGAGGAGGAAGATGAGGAGGAG                     2281
AGGGGAGGAAGCAGTCCGGGGGTGTGTGTGTGGACCCTTTGACTCTTCTGTCTG                     2335
ACCACCTGCCGCCTCTGCCATCGGACATGACGGAAGGACCTCCTTTGTGTTTTG                     2389
TGCTCCGTCTCTGGTTTTCTGTGCCCCGGCGAGACCGGAGAGCTGGTGACTTTG                     2443
GGGACAGGGGGTGGGGCGGGGATGGACACCCCTCCTGCATATCTTTGTCCTGTT                     2497
ACTTCAACCCAACTTCTGGGGATAGATGGCTGGCTGGGTGGGTAGGGTGGGGTG                     2551
CAACGCCCACCTTTGGCGTCTTGCGTGAGGCTGGAGGGGAAAGGGTGCTGAGTG                     2605
TGGGGTGCAGGGTGGGTTGAGGTCGAGCTGGCATGCACCTCCAGAGAGACCCAA                     2659
CGAGGAAATGACAGCACCGTCCTGTCCTTCTTTTCCCCCACCCACCCATCCACC                     2713
CTCAAGGGTGCAGGGTGACCAAGATAGCTCTGTTTTGCTCCCTCGGGCCTTAGC                     2767
TGATTAACTTAACATTTCCAAGAGGTTACAACCTCCTCCTGGACGAATTGAGCC                     2821
CCCGACTGAGGGAAGTCGATGCCCCCTTTGGGAGTCTGCTAACCCCACTTCCCG                     2875
CTGATTCCAAAATGTGAACCCCTATCTGACTGCTCAGTCTTTCCTCCTGGGAA                      2929
AACTGGCTCAGGTTGGATTTTTTCCTCGTCTGCTACAGAGCCCCCTCCCAACT                      2983
CAGGCCCGCTCCCACCCCTGTGCAGTATTATGCTATGTCCCTCTCACCCTCACC                     3037
CCCACCCCAGGCGCCCTTGGCCGTCCTCGTTGGGCCTTACTGGTTTTGGGCAGC                     3091
AGGGGGCGCTGCGACGCCCATCTTGCTGGAGCGCTTTATACTGTGAATGAGTGG                     3145
TCGGATTGCTGGGTGCGCCGGATGGGATTGACCCCAGCCCTCCAAAACTTTCC                      3199
CTGGGCCTCCCCTTCTTCCACTTGCTTCCTCCCTCCCCTTGACAGGGAGTTAGA                     3253
CTCGAAAGGATGACCACGACGCATCCCGGTGGCCTTCTTGCTCAGGCCCCAGAC                     3307
TTTTTCTCTTTAAGTCCTTCGCCTTCCCCAGCCTAGGACGCCAACTTCTCCCCA                     3361
CCCTGGGAGCCCCGCATCCTCTCACAGAGGTCGAGGCAATTTTCAGAGAAGTTT                     3415
TCAGGGCTGAGGCTTTGGCTCCCCTATCCTCGATATTTGAATCCCCAAATATTT                     3469
TTGGACTAGCATACTTAAGAGGGGCTGAGTTCCCACTATCCCACTCCATCCAA                      3523
TTCCTTCAGTCCCAAAGACGAGTTCTGTCCCTTCCCTCCAGCTTTCACCTCGTG                     3577
AGAATCCCACGAGTCAGATTTCTATTTTTAATATTGGGGAGATGGGCCCTACC                      3631
GCCCGTCCCCGTGCTGCATGAACATTCCATACCCTGTCCTGGGCCCTAGGTT                       3685
CCAAACCTAATCCCAAACCCCACCCCCAGCTATTTATCCCTTTCCTGGTTCCCA                     3739
AAAAGCACTTATATCTATTATGTATAAATAAATATATTATATATGAGTGTGCGT                     3793
GTGTGTGCGTGTGCGTGCGTGCGTGCGTGCGAGCTTCCTTGTTTTCAAGT                         3847
GTGCTGTGGAGTTCAAAATCGCTTCTGGGGATTTGAGTCAGACTTTCTGGCTGT                     3901
CCCTTTTTGTCACCTTTTTGTTGTTGTCTCGGCTCCTCTGGCTGTTGGAGACAG                     3955
TCCCGGCCTCTCCCTTTATCCTTTCTCAAGTCTGTCTCGCTCAGACCACTTCCA                     4009
ACATGTCTCCACTCTCAATGACTCTGATCTCCGGTCTGTCTGTTAATTCTGGAT                     4063
TTGTCGGGGACATGCAATTTTACTTCTGTAAGTAAGTGTGACTGGGTGGTAGAT                     4117
TTTTTACAATCTATATCGTTGAGAATTC                                              4145
```

FIG.2B

TRANSDOMINANT NEGATIVE PROTO-ONCOGENE

This invention was made with Government support under NIH R35 CA 44360 awarded by the National Institutes of Health. The Government has certain rights in the invention. This is a continuation of application Ser. No. 07/710,862 filed on Jun. 10, 1991, now abandoned.

BACKGROUND OF THE INVENTION

1. Field of The Invention

This invention relates to unique proto-oncogene sequences derived using recombinant DNA technology and to the production and use of these sequences as well as the expression products thereof.

2. Related Art

Advances in recombinant DNA technology have led to the discovery of normal cellular genes (proto-oncogenes) which control growth, development, and differentiation. Under certain circumstances, regulation of these genes is altered and they become oncogenes which cause normal cells to assume neoplastic growth behavior. There are approximately 40 known proto-oncogenes to date, which fall into various categories depending on their functional characteristics. These-include, (1) growth factors and growth factor receptors, (2) messengers of intracellular signal transduction pathways, for example, between the cytoplasm and the nucleus, and (3) regulatory proteins influencing gene expression and DNA replication.

Several oncogenes and proto-oncogenes are known to encode more than one product by using alternatively spliced mRNAs. These include the SV40 T antigen gene, c-src, c-Ha-ras, c-abl and c-myb. Alternative splicing includes or excludes particular coding sequences within the mRNA, which is eventually translated. Consequently, the biological function of a single gene can be expanded by the splicing choice. Previous reports have shown that an alternatively spliced c-myb mRNA encodes a truncated form of the c-myb p75 which includes the DNA binding region and nuclear localization signal present in c-myb protein, but lacks regulatory regions required for transcriptional activation (Weber, et al., Science, 249:1291, 1990). The truncated protein has been shown to interfere with the function of c-myb during differentiation of mouse erythroid leukemia cells.

Many proteins cooperate with each other in the activation of transcription from specific promoters. Through this cooperation, the gene can be transcribed and a protein product generated. Members of the Fos proto-oncogene family, along with members of the Jun gene family, form stable complexes which bind to DNA at a specific site designated AP-1. The AP-1 site is located in the promoter region of a large number of genes. Binding of the Fos/Jun complex activates transcription of a gene associated with an AP-1 site. In cells that have lost their growth regulatory mechanisms, it can be envisioned that this Fos/Jun complex may "sit" on the AP-1 site, causing over expression of a particular gene. Since many cell proliferative disorders result from the over expression of an otherwise normal gene, such as a proto-oncogene, it would be desirable to identify methods which interfere with the excessive activation of these genes.

For many years, various drugs have been tested for their ability to alter the expression of genes or the translation of their messages into protein products. One problem with existing drug therapy is that it tends to act indiscriminately and affect healthy cells as well as neoplastic cells. This is a major problem with many forms of chemotherapy where there are severe side effects primarily due to the action of the toxic drugs on healthy cells.

In view of the foregoing, there remains a need for therapeutic agents which specifically inhibit the over expression of genes associated with cell-proliferative disorders, but have limited negative effects on healthy cells.

SUMMARY OF THE INVENTION

The initial response of a cell to an external stimulus results in the induction of a select set of genes, many of which are nuclear proto-oncogenes. Prominent among the products of these early response genes are Fos and Jun which serve as a paradigm for cooperation between oncoproteins to activate transcription of specific promoters. The Fos and Jun proteins bind to AP-1 sites as heterodimers. The heterodimeric complex activates transcription of genes containing AP-1 binding sites.

During study of the FosB gene, a surprising means of regulating transcription was discovered. It was found that a truncation of FosB, which occurs by deletion of a region of an exon which encodes a trans-activation domain, results in a trans-repressing protein which causes suppression of promoters containing the AP-1 site.

In a first aspect, the present invention relates to a polynucleotide encoding a trans-repressing protein of the Fos gene family characterized as encoding a protein (1) having a leucine zipper domain, and (2) forming a heterodimer with a Jun related protein, wherein the heterodimer is capable of binding to an AP-1 site and suppressing transcriptional transactivation of a promoter containing the AP-1 site.

In a second aspect, the present invention relates to a trans-repressing protein encoded by polynucleotide of the invention.

In a further aspect, the present invention relates to a method of treating a cell proliferative disorder wherein the disorder is associated with activation of a promoter containing an AP-1 site which comprises (1) removing a sample of tissue associated with the disorder from a subject with the disorder, (2) isolating from the tissue sample a hematopoietic cell which has infiltrated the tissue, (3) contacting the hematopoietic cell with a recombinant expression vector comprising a polynucleotide encoding the Fos protein of the invention, and (4) introducing the hematopoietic cell into the subject.

BRIEF DESCRIPTION OF THE DRAWINGS

FIGS. 1a and 1b shows the structure of FosB2 coding sequence. In (A), FosB2 coding region is aligned with FosB cDNA. The entire coding sequence from nucleotide 1202 to 2218 (based on numbering system in Zerial, et al., EMBO J., 8:805, 1989) including the intron-derived exon from 1913 to 2052 (the hatched box), is shown. The stop codon (TGA) in FosB2 reading frame is indicated. BR box represents the basic region, and L—L—L—L—L box indicates the "leucine zipper". In FIG. 1(B), the sequence of the alternative spliced intron of FosB gene is shown. Nucleotide sequence of mouse genomic DNA surrounding the alternative intron of FosB gene is shown in the top line. FosB and FosB2 cDNA sequences are aligned and presented in the middle line and bottom line, respectively. The conserved splicing donor (GT) and acceptor (AG) are boldfaced. The consensus branch point sequence (CTGAC) and a pyrimidine stretch which is involved in lariat formation are underlined. The stop codon (TGA) of FosB2 cDNA is also underlined, (...) indicates complete identity.

FIG. 2A and 2B shows mouse FosB DNA and deduced amino acid sequences.

DETAILED DESCRIPTION OF THE PREFERRED EMBODIMENT

Jun and Fos proteins play an important role in the regulation of gene expression in many cell types. Known Jun proteins include c-Jun, JunB and JunD. Fos and Jun proteins contain a distinctive "leucine zipper" domain which enables members of both families to form heterodimers and subsequently bind to AP-1 sites. The heterodimer, once bound, activates transcriptional transactivation of a promoter containing an AP-1 site. Cooperation between these two nuclear oncoproteins is required for efficient transcriptional activation of the gene associated with the AP-1 site.

In contrast to the foregoing, the present invention relates to a new member of the Fos gene family which is a trans-repressing protein designated FosB2. This protein is a truncated form of FosB. Although FosB2 associates with a Jun protein to form heterodimers which bind to AP-1 sites, these FosB2 containing heterdoimers are unable to transactivate transcription.

FosB2, is a trans-acting molecule which has a negative regulatory activity. A trans-activating locus commonly refers to a DNA sequence which encodes a molecule that affects another DNA sequence located on a chromosome different from the trans-activating locus. Instead of functioning to activate transcription at a particular site in the DNA, FosB2 acts to negatively affect transcription, perhaps by sequestering the Jun protein and thereby interfering with positive regulatory elements.

Other proteins regulating gene expression have been found which apparently "zip" together in pairs. The formation of this stable complex is required before the proteins can effectively bind to a specific region of DNA. The area of the zipper where the proteins associate is rich in periodically spaced leucine residues, thus the term "leucine zipper". Regions of certain proteins contain a leucine residue at every seventh position of an alpha helix which, through hydrophobic interactions, enables the proteins to form dimers. The trans-repressing FosB2 described in the present invention contains a classical leucine zipper domain. This allows FosB2 to form a complex with proteins of the Jun family, which also contain a leucine zipper domain. This leucine zipper structure is found in various transcription factors such as Fos, Myc, and Jun; the yeast transcription factors GCN4 and yAP-1, enhancer binding protein (C/EBP), and cAMP responsive element-binding protein (CREB). The FosB2 protein of the present invention associates with known Jun proteins encoded by c-Jun, JunB and JunD, however, FosB2 can also associate with other proteins containing a Jun related leucine zipper to negatively regulate transcription.

Association of FosB2 with members of the Jun family or other protein containing a Jun related leucine zipper is necessary for binding to DNA. While the trans-repressing protein of the invention, complexed with a member of the Jun family, preferably binds to an AP-1 site, it may alternatively bind to another site containing the consensus sequence found within AP-1.

Genomic DNA encoding FosB2 protein contains interrupting sequences (introns) and coding sequences (exons). The truncation event which results in FosB2 is caused by a deletion of 140 base pairs from an exon of the FosB gene. This deletion of coding sequence from nucleotides 1913 through 2052 results from alternative splicing wherein the entire FosB gene is initially transcribed into one entire mRNA which is subsequently cut such that only RNA sequences on either side of the cut remain. As a result, the biological function of the FosB gene is expanded by the splicing event. In FosB2, an exon encoding a trans-activation domain is spliced out of FosB mRNA, thereby creating FosB2 which lacks trans-activating activity. However, although unable to transactivate transcription, FosB2 retains both the DNA binding and the leucine zipper domain and, as such, can still complex with Jun family proteins. These FosB2/Jun complexes can still bind to promoters with AP-1 sites, but are unable to transactivate the cell. Consequently, FosB2 acts as a regulatory factor by negatively affecting the transcription of genes containing AP-1 sites. In addition, FosB2 interferes with the transforming ability of FosB and other members of the Fos gene family by competing with Jun proteins in the formation of FosB/Jun complexes.

The invention provides polynucleotides encoding the FosB2 trans-repressing protein. These polynucleotides include DNA, cDNA and RNA sequences which encode transrepressing protein. It is understood that all polynucleotides encoding all or a portion of FosB2 are also included herein, so long as they exhibit the trans-repressing activity of FosB2. Such polynucleotides include both naturally occurring and intentionally manipulated, for example, mutagenized polynucleotides.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences and 2) antibody screening of expression libraries to detect shared structural features.

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

A FosB2 cDNA library can be screened by injecting the various cDNAs into oocytes, allowing sufficient time for expression of the cDNA gene products to occur, and testing for the presence of the desired cDNA expression product, for example, by using antibody specific for FosB2 polypeptide or by using functional assays for FosB2 binding activity.

Alternatively, a cDNA library can be screened indirectly for FosB2 peptides having at least one epitope using antibodies to FosB2. Such antibodies can be either polyclonally or monoclonally derived and used to detect expression product indicative of the presence of FosB2 cDNA.

The development of specific DNA sequences encoding FosB2 can also be obtained by: (1) isolation of a double-stranded DNA sequence from the genomic DNA; (2) chemical manufacture of a DNA sequence to provide the necessary codons for the polypeptide of interest; and (3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the use of genomic DNA isolates (1), is the least common. This is especially true when it is desirable to obtain the microbial expression of mammalian polypeptides because of the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNNDNA hybridization procedures which are carried out on cloned copies of the cDNA which have been denatured into a single-stranded form (Jay, et al., *Nucleic Acid Research*, 11:2325, 1983).

DNA sequences encoding FosB2 can be expressed in vitro by DNA transfer into a suitable host cell. "Recombinant host cells" or "host cells" are cells in which a vector can be propagated and its DNA expressed. The term also includes any progeny of the subject host cell. It is understood that not all progeny are identical to the parental cell since there may be mutations that occur at replication. However, such progeny are included when the terms above are used.

Host cells may also include yeast. cDNA can be expressed in yeast by inserting the cDNA into appropriate expression vectors and introducing the product into the host cells. Various shuttle vectors for the expression of foreign genes in yeast have been reported (Heinemann, et al., *Nature*, 340:205, 1989; Rose, et al., *Gene*, 60:237, 1987). DNA sequences encoding FosB2 can be expressed in vivo in either prokaryotes or eukaryotes. Methods of expressing DNA sequences having eukaryotic coding sequences in prokaryotes are well known in the art. Biologically functional viral and plasmid DNA vectors capable of expression and replication in a host are known in the art. Such vectors are used to incorporate DNA sequences of the invention. Hosts include microbial, yeast and mammalian organisms.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell.

When the host is a eukaryote, such methods of transfection of DNA as calcium phosphate co-precipitates, conventional mechanical procedures such as microinjection, insertion of a plasmid encased in liposomes, or virus vectors may be used. Eukaryotic cells can also be cotransformed with foreign cDNA encoding FosB2 protein, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982).

Isolation and purification of microbially expressed protein, or fragments thereof, provided by the invention, may be carried out by conventional means including preparative chromatography and immunological separations involving monoclonal or polyclonal antibodies.

Antibodies provided in the present invention are immunoreactive with FosB2 protein. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et a., *Nature*, 256:495, 1975; *Current Protocols in Molecular Biology*, Ausubel, et al., ed., 1989).

Minor modifications of FosB2 primary amino acid sequence may result in proteins which have substantially equivalent activity compared to the FosB2 proteins described herein. Such modifications may be deliberate, as by site-directed mutagenesis, or may be-spontaneous. All proteins produced by these modifications are included herein as long as FosB2 activity exists.

In the present invention, the FosB2 sequences may be inserted into a recombinant expression vector. The term "recombinant expression vector" refers to a plasmid, virus or other vehicle known in the art that has been manipulated by insertion or incorporation of FosB2 genetic sequences. Such expression vectors contain a promotor sequence which facilitates the efficient transcription of the inserted genetic sequence in the host. The expression vector typically contains an origin of replication, a promoter, as well as specific genes which allow phenotypic selection of the transformed cells.

The present invention also provides gene therapy for the treatment of cell proliferative disorders which are mediated by Fos/Jun protein complexes. Such therapy would achieve its therapeutic effect by introduction of the FosB2 polynucleotide, into cells of animals having the proliferative disorder. Delivery of FosB2 polynucleotide can be achieved using a recombinant expression vector such as a chimeric virus or a colloidal dispersion system.

The term "cell-proliferative disorder" denotes malignant as well as nonmalignant cell populations which morphologically often appear to differ from the surrounding tissue. For example, the FosB2 polynucleotide is useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine, and cancer of the esophagus. The FosB2 polynucleotide is also useful in treating non-malignant cell-proliferative diseases such as psoriasis, pemphigus vulgaris, Behcet's syndrome, and lipid histiocytosis. Essentially, any disorder which is etiologically linked to the formation of the Fos/Jun family heterodimer would be considered susceptible to treatment with FosB2 polynucleotide.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), HaNey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a FosB2 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the FosB2 polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA 12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retrovital virions.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for FosB2 polynucleotides a colloidal dispersion system. Colloidal dispersion systems include macromolecule complexes, nanocapsules, microspheres, beads, and lipid-based systems including oil-in-water emulsions, micelies, mixed micelies, and liposomes. The preferred colloidal system of this invention is a liposome. Uposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoyiphosphatidyicholine and distearoylphosphatidylcholine.

The targeting of liposomes has been classified based on anatomical and mechanistic factors. Anatomical classification is based on the level of selectivity, for example, organ-specific, cell-specific, and organeile-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to as tumor-associated antigens (TAAs), may be exploited for the purpose of targeting antibody-FosB2-containing liposomes directly to the malignant tumor. Since the FosB2 gene product may be indiscriminate with respect to cell type in its action, a targeted delivery system offers a significant improvement over randomly injecting nonspecific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Uposomes may also be targeted to cells expressing receptors for hormones or other serum factors.

The invention also provides a method for suppressing the transcriptional transactivation of a promoter containing an AP-1 site by contacting the AP-1 site with an effective amount of the trans-repressing protein. An effective amount is meant to include that level which results in the deactivation of a previously activated promoter containing AP-1. The amount of FosB2 transrepressing protein required would be that amount necessary to displace Fos protein in an existing Fos/Jun complex in the cell, or that amount necessary to compete with Fos protein to form complexes with the various Jun proteins. By functionally inactivating the Fos/Jun complex, both transcription and transformation can be suppressed. Delivery of an effective amount of the trans-repressing protein can be accomplished by one of the mechanisms previously described, such as by retroviral vectors or liposomes, or other methods well known in the art.

In addition, the invention discloses a method of treating cell proliferative disorders, by removal of a tissue sample from a subject with the disorder; isolating hematopoietic cells from the tissue sample; and contacting isolated cells with a recombinant expression vector containing DNA encoding FosB2 protein and, optionally, a target specific gene. Optionally, the cells can be treated with a growth factor, such as interleukin-2, to stimulate cell growth, before reintroducing the cells into the subject. When reintroduced, the cells will specifically target the cell population from which they were originally isolated. In this way, the trans-repressing activity of FosB2 may be used to inhibit undesirable cell proliferation in a subject.

An alternative use for recombinant retroviral vectors comprises the introduction of polynucleotide sequences into the host by means of skin transplants of cells containing the virus. Long term expression of foreign genes in implants, using cells of fibroblast origin, may be achieved if a strong housekeeping gene promoter is used to drive transcription. For example, the dihydrofolate reductase (DHFR) gene promoter may be used. Cells such as fibroblasts, can be infected with virions containing a retroviral construct containing the gene of interest, for example FosB2, together with a gene which allows for specific targeting, such as TAA, and a strong promoter. The infected cells can be embedded in a collagen matrix which can be grafted into the connective tissue of the dermis in the recipient subject. As the retrovirus proliferates and escapes the matrix it will specifically infect the target cell population. In this way the transplantation results in increased amounts of trans-repressing FosB2 being produced in cells manifesting the cell proliferative disorder.

Because the present invention identifies a nucleotide sequence expressed in FosB, but not in FosB2, it is possible to design appropriate therapeutic or diagnostic techniques directed to this unique sequence of FosB. Thus, where a cell-proliferative disorder is associated with the expression of FosB, the unique sequence associated with FosB, but not with FosB2, could be used to produce nucleic acid sequences that interfere with FosB expression at the translational level. This approach utilizes, for example, antisense nucleic acid and ribozymes to block translation of a specific FosB mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target FosB-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Antisense sequences can be therapeutically administered by techniques as those described above for the administration of FosB2 polynucleotides. Especially preferred for therapeutic delivery of antisense sequences is the use of targeted liposomes.

The following examples are intended to illustrate but not limit the invention. While they are typical of those that might be used, other procedures known to those skilled in the art may alternatively be used.

EXAMPLE 1

FosB2 cDNA CLONING

FosB2 cDNA which contains the entire coding sequence was obtained during cloning of the FosB cDNA by polymerase chain reaction (PCR) (Sherman, et al., TIG, 5:137, 1989). Primers corresponding to nucleotides (NT) 1284–1301 and 2212–2227 of the published sequence (Zerial, et al., EMBO J., 8:805–813, 1989) were used to clone FosB cDNAs using PCR. Multiple independent clones were selected and analyzed by nucleotide sequencing.

Characterization of FosB2 cDNA

During the process of molecular cloning of FosB cDNA by PCR using oligonucleotides based on the published FosB sequence (Zerial, et al., EMBO J., 8:805–813, 1989), DNA fragments of approximately 0.9 to 1.0 kbp were obtained.

These cDNA fragments were subcloned and when the nucleotide sequence of the fragments was determined, it became apparent that many of them were missing 140 bp as compared to previously described FosB cDNAs. More importantly, the open reading frame of the shorter cDNA could encode a protein of only 237 aa as compared to the 338 aa protein encoded by the FosB cDNA.

FIG. 1 schematically illustrates the molecular structure of both the FosB and the shorter cDNA termed FosB2. The entire coding sequence from nucleotide 1202 to 2218 (based on numbering system in Zerial, et al., supra) including the intron-derived exon from 1913 to 2052 (the hatched box), is shown.

The nucleotide and deduced amino acid sequence of the first 237 aa of the two proteins are identical (Zerial, et al., EMBO J., 8:805–813, 1989). Examination of the sequences of FosB and FosB2 cDNA revealed that the FosB2 protein terminates immediately following the 140 bp deletion. Thus, the remaining sequence in the 3' region of FosB2 is identical to FosB but cannot be translated in this frame. The FosB2 protein, however, does contain the leucine zipper domain (aa 183 to 211) and the basic region (aa 157 to 182), which is well conserved among all members of the Fos family (Matsui, et al., Oncogene, 5:249–255, 1990).

The nucleotide sequence of a corresponding FosB genomic DNA fragment was determined to address the question of the nature of the 140 bp insert in FosB. A comparison of the sequences of FosB genomic DNA, and FosB and FosB2 cDNAs revealed that the 140 bp insert has all the hallmarks of a bonafide type II intron. In addition to the consensus splice donor (AG↓GTGAGA) and acceptor (CAG) sites, there are potential branch points 23 and 28 NT from the AG and a pyrimidine-rich stretch between branch point and splice site. Because the 140 bp intron is deleted in FosB2, the reading frame shifts by −1, creating the stop codon TGA. Therefore, FosB2, the product of spliced FosB mRNA, is only 237 aa long.

EXAMPLE 2

PLASMID DNA CONSTRUCTION AND RNase PROTECTION ANALYSIS

Plasmid SK-FosB2 contains the entire FosB coding sequence except the intron-derived exon, in the vector SK. Plasmid SK-FosB contains the entire FosB coding sequence. pBKFosB and pBKFosB2 are expression constructs of FosB and FosB2 in the FBJ-LTR driven expression vector pBKPL. The analogous c-Fos expression plasmid pBK28, and the c-jun expression plasmid pSV-c-jun have been described (Lamph, et al., Nature, 334:629–631, 1988; Sassone-Corsi, et al., Cell, 54:553–560, 1988).

Southern blotting analysis of genomic DNA suggested the presence of a single FosB gene. RNA was prepared from cells induced with serum by methods known in the art, and hybridized to FosB2 probe. Within 60 minutes following serum induction, maximal levels of a 5.0 kb species of RNA was detected. Because the alternative spliced form of FosB RNA is shorter by 140 bp, the analysis performed here was not able to distinguish between the two forms of RNA. To confirm the existence of alternatively spliced forms of FosB mRNAs, RNase protection analysis was performed using probes generated from either FosB2 or FosB cDNA. Upon annealing with full length FosB mRNA and subsequent RNase digestion, a 166 NT fragment diagnostic for FosB RNA was observed. Other probes used in RNase protection assays included a FosB NcoI fragment which is 835 NT. This probe protected the expected 784 NT FosB fragment. In addition, the same probe yielded 478 NT and 166 NT bands, representative of FosB2 and the 140 bp deletion.

Five µg of cytoplasmic RNA were subjected to RNA blot analysis. FosB2 coding region of cDNA was used as the hybridization probe. Uniformly $^{32}$P-UTP-labeled complementary RNA probes were synthesized. Results showed coordinated regulation of FosB and FosB2 mRNA by serum in the absence and presence of cyclohexamide in NIH 3T3 fibroblasts.

For precise quantitation of the abundance of two species of RNAs, analysis was performed using probes generated from FosB cDNA. In cells stimulated with serum, appropriate length FosB and FosB2 specific fragments were identified. From densitometric scanning of the band intensity, length of fragments, and uracil content of fragments, it appeared that FosB2 was slightly more abundant (FosB/FosB2=$^{0.83}$/$_1$) than FosB mRNA.

The results indicated that (i) bands of the expected sizes corresponding to FosB and FosB2 RNA were identified, (ii) FosB and FosB2 expression was stimulated by serum and (iii) induction of FosB and FosB2 mRNA by serum was superinduced with cycloheximide. No induction of FosB or FosB2 mRNA was detected when the cells were treated with tetradecanoyl phorbol 13-acetate (TPA). FosB is thus unique among early response genes in that it is inducible with serum, but not TPA.

EXAMPLE 3

PROTEIN ANALYSIS BY IMMUNOPRECIPITATION

NIH 3T3 cells were starved with 0.5% bovine calf serum for 2 days, and then stimulated with 10% dialyzed calf serum in the presence of methionine- and cysteine-free media. Forty minutes before harvest, the cells were labeled with $^{35}$S-methionine (200 µCi/ml and cell lysates were prepared (Barber, et al., Mol. Cell. Biol., 7:2201–2211, 1987). Lysates containing equal amounts of protein were used for immunoprecipitation with anti-FosB specific antibody 5108-1B (against FosB peptide residues from 80 to 97) or a c-Fos monoclonal antibody 18H6.

Several extensively phosphorylated forms of c-Fos protein were immunoprecipitated with 18H6. Maximum levels of precipitated protein were obtained between 30–60 minutes following serum induction and a marked decrease was observed at 120 minutes. No Jun related proteins were identified since the extracts were boiled prior to immunoprecipitation which disrupted the Fos-Jun complex. In parallel experiments, 5108-1B antiserum immunoprecipitated three polypeptides of approximate molecular weight of 65 kD, 55 kD, and 43 kD, after serum induction. These polypeptides were identified in quiescent cells, but the levels increased by 40 minutes and declined to basal levels by 90–120 minutes following serum induction. When the antibody was preincubated with synthetic peptide against which the antisera was raised, two of the polypeptides were not detected. On the other hand, the immunoprecipitation of these two polypeptides was not affected if the antisera were preincubated with a non-specific peptide (aa 152 to 176 of murine c-Rel) originating from c-Rel protein. Neither the 65 or 55 kD polypeptides was observed with the pre-immune sera. Since there is not an antisera which distinguishes between FosB and FosB2 at present, it cannot be determined as to which of the two polypeptides is the product of FosB or FosB2 RNAs. However, both polypeptides, as well as in vitro translated FosB protein, show common peptides following digestion with V8 protease. From the molecular weights of the in vitro translated FosB and FosB2 RNA transcripts and the possible posttranslational modifications, the 65 kD polypeptide is FosB and the 55 kD polypeptide Fos B2. The lower band was non-specifically precipitated by protein A sepharose and was not blocked by FosB peptide. It is likely that this lowest molecular weight band is actin, which is inducible with serum and migrates at a position of about 43 kD.

EXAMPLE 4

IN VITRO TRANSCRIPTION AND TRANSLATION

T7-c-Fos, pGEM-c-Jun, SK-FosB and SK-FosB2 were all linearized with EcoRI and transcribed with T7 polymerase or T3 polymerase. Each RNA was translated with micrococcal nuclease-treated, methionine-free rabbit reticulocyte lysate as directed by the supplier (Promega, Madison, WI). For gel shift assays, equal molar amounts of unlabeled proteins were combined, and incubated with $^{32}$P-γTP labeled TRE/AP-1 oligonucleotide at room temperature for 15 minutes and the binding complex formation was analyzed on a native 4% acrylamide gel (Sassone-Corsi, et al., *Nature*, 336:692–695, 1988; Dwarki, et al., EMBO J., 9:225,232, 1990).

FosB2 binds to AP-1 site

A hallmark of the members of the Fos gene family is that their products form heterodimers with members of Jun family and bind to AP-1 sites. In vitro translated FosB2 and c-Jun was found to bind efficiently to an AP-1 site. Competition with excess unlabeled oligonucleotide containing the cognate AP-1 site abolished binding. Little or no binding was observed with either FosB2, FosB, c-Fos or c-Jun alone. To confirm that DNA binding by the FosB2-c-Jun complex was dependent on heterodimer formation via the leucine zipper domain, RNAs encoding FosB2 and a c-Jun mutant containing a deletion of the leucine zipper were cotranslated in vitro (Ransone, et al., *Genes Dev.*, 3:770–781, 1989). No binding to the AP-1 site was detected.

FosB2 can efficiently bind to an AP-1 site in association with c-Jun. Various combinations of expression plasmids for FosB, FosB2, and c-Jun (pBKFosB, pBKFosB2, pSVc-jun and pBK28) along with a reporter plasmid 5XTRE-TKCAT, which contains five copies of the TPA-responsive element (TRE) linked to a CAT reporter gene, were cotransfected into F9 teratocarcinoma cells to determine whether FosB2 in association with Jun could cause transcriptional transactivation of promoters containing AP-1 binding sites. Briefly, embryonic carcinoma F9 cells were plated in 10 cm dishes at a density of 5×10⁶ cells/plate 24 hours before transfection. Transfection protocol was as described (Chen, et al., *Mol. Cell. Biol.*, 7:2745–2752, 1987) and β-galactosidase activity was assayed by the CNPG reaction (Nielsen, et al., *Proc. Natl. Acad. Sci. USA*, 80:5198–5202, 1983). Two μg of the reporter construct 5XTRECAT and 2 μg of pBAG (a β-galactosidase expression plasmid, which served as an internal control of transfection efficiency) were cotransfected into F9 cells with various combinations of expression plasmids.

For CAT assays, cell extracts containing equal β-GAL activity were incubated with $^{14}$C-chloramphenicol, and the reaction products were analyzed on TLC plates as described (Gorman, et al., *Mol. Cell. Biol.*, 2:1044–1051, 1982). Forty-eight hours after transfection, CAT activity was measured. All CAT activity assays were standardized with β-galactosidase activity. Fold induction was standardized with the control reaction (no expression plasmid) and three independent experiments were performed. c-Jun (0.5 μg) was cotransfected with 0–12 μg of c-Fos, FosB, or FosB2 expression plasmid.

Like c-Fos, FosB was able to transactivate transcription in cooperation with c-Jun. FosB2 on the other hand was unable to transactivate transcription. Because FosB2 can form heterodimers with c-Jun and bind to AP-1 site, it apparently interferes with transcriptional activation by c-Fos or FosB proteins. Upon increasing the concentration of transfected FosB2 plasmid, the transactivation by c-Fos was incrementally reduced. FosB2 also appeared to suppress transcriptional transactivation by FosB. When the amount of c-Fos DNA was increased to 12 μg or addition of 6 μg of FosB DNA, instead of FosB2 DNA, CAT activity increased. This indicated that reduced CAT activity upon addition of FosB2 plasmid was not due to adventitious events like squelching. Furthermore, immunostaining of the transfected cells with c-Fos monoclonal antibody (18H6) showed that c-Fos protein was synthesized. Finally, FosB2 mutants in the leucine zipper domain were unable to suppress transactivation by c-Fos and c-Jun. Thus, the results show that FosB2 can interfere with transcriptional transactivation by Fos proteins such as c-Fos and FosB.

EXAMPLE 5

FosB2 SUPPRESSES TRANSFORMATION BY Fos PROTEINS

Increasing amounts of FosB2 plasmid decreased the transforming potential of v-Fos, c-Fos, and FosB proteins, as seen in Table 1. In agreement with previous results, v-Fos is a more potent transforming agent than its cellular cognate, c-Fos (Miller, et al., *Cell*, 36:51–60, 1984). Surprisingly, however, FosB appeared to have a transforming potential equivalent to that of the v-Fos gene. These results also emphasize a link between transactivation potential and cellular transformation by Fos proteins.

208F cells were transfected with 2 μg of transforming plasmid DNA (v-Fos, c-Fos, or FosB) along with different amounts of a FosB2 expression plasmid (from 0–16 μg); the total amount of DNA used in each transfection was kept constant by varying the amount of carrier DNA. Focus assays were performed as previously described (Miller, et al., *Cell*, 36:51–60, 1984). Each transfection was plated in duplicate. Foci were counted 12 days after transfection for v-Fos transfected cells, and 17 days after transfection for c-Fos and FosB transfected cells. FosB2 interfered with both the transcriptional transactivation and transformation potential of c-Fos and FosB, suggesting a role as a trans-negative regulator.

TABLE 1

| Transforming DNA (2 μg) | FosB2 (μg) | Number of Foci | | Transformation Efficiency (Average) |
|---|---|---|---|---|
| | | Expt. 1 | Expt. 2 | |
| v-Fos | 0 | 130/108 | 55/67 | 100 |
| | 2 | 58/75 | 30/48 | 60 |
| | 16 | 36/38 | 9/15 | 25 |
| c-Fos | 0 | 43/31 | 21/26 | 100 |
| | 2 | 16/8 | 5/3 | 17 |
| | 16 | 2/8 | 5/2 | 15 |
| FosB | 0 | 163/175 | 48/61 | 100 |

TABLE 1-continued

| Transforming DNA (2 µg) | FosB2 (µg) | Number of Foci | | Transformation Efficiency (Average) |
|---|---|---|---|---|
| | | Expt. 1 | Expt. 2 | |
| | 2 | 102/82 | 43/25 | 51 |
| | 16 | 38/36 | 28/17 | 31 |
| None | 16 | 0/0 | 0/0 | |

EXAMPLE 6

IN VIVO EXPRESSION OF RETROVIRAL MEDIATED GENE TRANSFER IN IMPLANTS

Although the following example is directed to chimeric retroviral expression in mice, the techniques described herein are readily modified for use with other species, such as humans. In practice, the retroviral vectors of the invention containing FosB2 polynucleotide would further contain a gene which would express a binding protein or some other ligand which, upon release of the retrovirus from the implant, would allow the retrovirus to specifically target a particular cell type. Those of skill in the art can readily make such modifications without resorting to undue experimentation.

Animal and cell culture Conditions

Adult male C57 BL/6J mice (6–8 weeks old) and Nu/Nu athymic mice can be obtained from the Jackson Laboratory, ME. The retroviral packaging cell lines Ψ-CRE and Ψ-CRIP (Danos, et al., *Proc. Natl. Acad. Sci.* USA, 85:6460–6464, 1988) and the cell lines NIH 3T3 and rat 208F are maintained in Dulbecco's Modified Eagle's Medium (DMEM) supplemented with 10% bovine calf serum. Primary fibroblasts are obtained from day 17 embryos of C57 BL/6J mice and are grown in DMEM supplemented with 10% fetal calf serum. Infected cells are then selected in medium containing 400 µg/ml of G418.

Vector Construction

Retroviral vectors such as LNCdF9L can be used for the vector construction (Axelrod, et al., *Proc. Natl. Acad. Sci.*, 87:5173–6177, 1990). The vectors are generated by inserting a 3.1 kBP Bam H1 fragment containing the entire coding sequence of the β-galactosidase gene, for example, into the Bgl II site of plasmid LNL-SLX to generate the vector LNL-SLXβgal. The LNL-SLX vector is a derivative of LNL-XHC (Bender, et al., *J. Virology*, 61:1639–1646, 1987) and contains a new polylinker to increase the number of cloning sites. A 350 bp Hind III fragment of the mouse dihydrofolate reductase (DHFR) promoter can be cloned in the unique Hind III site of LNL-SLXβgal. A Bam HI/Hind III fragment containing the human intermediate early cytomegalovirus (CMV-IE) promoter (−522 to +55; Nelson, et al., *Mol. Cell. Biol.*, 7:4125–4129, 1987) can be cloned in the Bam HI/HindIII site of LNL-SLXβgal. The gene of interest (FosB2), along with a target-specific gene, can be cloned into the vector to generate target-specific vehicles for the FosB2 gene and its gene product.

Analysis of β-galactosidase activity

Beta-galactosidase histochemistry is performed according to Sanes, et al. (EMBO J., 5:3133, 1986) with minor modifications. Cultured cells are rinsed with phosphate buffered saline solution (PBS) pH 7.4 and then fixed for 5 minutes on ice in 2% formaldehyde plus 0.2% glutaraldehyde in PBS. The cells are then rinsed 2 times with PBS and overlaid with a solution containing 1 mg/ml 4-Cl-5-Br-3-indodyl-β-galactosidase (X-gal), 5 mM potassium ferricyanide, 5 mM potassium ferrocyanide and 2 mM $MgCl_2$ in PBS pH 7.4. Incubation is performed at 37° C. for 2 to 24 hours. To analyze β-galactosidase activity in the artificial collagen matrix, the fixation is prolonged for 30 minutes on ice.

Virus production

Ten µg of plasmid vector DNA is transfected into the ecotropic packaging cell line Ψ-CRE by the calcium phosphate co-precipitation method. Other packaging cell lines known in the art can alternately be used. The medium is changed 24 hours later and 48 hours after transfection, the culture medium is harvested and used to infect the amphotropic packaging cell line Ψ-CRIP, for example, in the presence of 8 µg/ml of polybrene. Single colonies of infected Ψ-CRIP cells are isolated by selection in the presence of G418-containing medium and expanded. Recombinant retroviruses are harvested from confluent culture dishes, filtered, and used to infect mouse embryo fibroblasts cells in the presence of polybrene to determine the viral titers. Twenty-four hours after infection, the medium is changed to G418 containing medium and colonies stained and counted after 12 to 14 days. The presence of helper virus is assayed by the marker residue method (Keller, et al., *Nature*, 318:149–154, 1985). Briefly, the medium from the infected cells is used to infect naive NIH 3T3 cells. The presence of β-galactosidase positive cells is determined after 72 hours and the presence of G418 resistant colonies is quantified after 14 days.

Implantation of infected mouse embryo fibroblasts in mice

Infected mouse embryo fibroblast cells are embedded in a collagen matrix as previously described (Louis, et al., *Proc. Natl. Acad. Sci.* USA, 85:3150–3154, 1988). The collagen matrix containing $2 \times 10^6$ infected fibroblasts is then grafted into the connective tissue of the dermis in the mid-back of recipient mice. To ensure rapid vascularization of the grafted tissue, a 2 $mm^2$ piece of gelfoam (Upjohn) containing 24 g of basic fibroblast growth factor is inserted into the connective tissue along with each graft (Louis, et al., id.) At different intervals of time, the implanted artificial collagen matrix is removed and stained for β-galactosidase activity.

Use of housekeeping gene promoters

Sustained expression in the implants may be a function of the type of the promoter used to initiate the transcription of the foreign gene. Since CMV is an inducible promoter and may require actively growing cells, a promoter which maintains the constitutive levels of many housekeeping genes is used. Retroviral vectors containing murine dihydrofolate reductase gene promoter, for example, and the bacterial β-galactosidase gene as a reporter are used. Clones producing high titre amphotropic recombinant viruses are selected by infecting NIH 3T3 cells, and analyzing for β-galactosidase activity and the presence of helper viruses as described in this example.

Further characterization of the recombinant viruses can be accomplished by analysis of the RNA transcripts from cells infected with the LNL-SLX β-gal viruses. Transcripts of the expected size will be detectable in virus-producing CRIP cells or mouse embryo fibroblasts. No transcripts will be detected in uninfected cells.

β-galactosidase expression in mice

Mouse embryo fibroblasts are infected with either LNL-SLX CMV β-gal or LNL-SLX DHFR β-gal viruses to test if the sustained expression of β-galactosidase can be attained in vivo. Infected cells are embedded in a collagen matrix and grafted in mice. After different time intervals, the grafts are explanted and analyzed for the presence of β-galactosidase positive cells by staining blue with X-Gal. A minimum of two to three grafts are explanted at each time point.

SUMMARY OF SEQUENCES

Sequence ID No. 1 is the nucleic acid sequence (and the deduced amino acid sequence) of a genomic fragment encoding a mouse-derived FosB protein.

Sequence ID No. 2 is the deduced amino acid sequence of a mouse-derived FosB protein.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4144 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: MouseFosB ( i x ) FEATURE:
        ( A ) NAME/KEY: CDS
        ( B ) LOCATION: 1202..2216

( x i ) SEQUENCE DESCRIPTION: SEQ ID NO:1:

```
ATAAATTCTT ATTTTGACAC TCACCAAAAT AGTCACCTGG AAAACCCGCT TTTTGTGACA      60
AAGTACAGAA GGCTTGGTCA CATTTAAATC ACTGAGAACT AGAGAGAAAT ACTATCGCAA     120
ACTGTAATAG ACATTACATC CATAAAAGTT TCCCCAGTCC TTATTGTAAT ATTGCACAGT     180
GCAATTGCTA CATGGCAAAC TAGTGTAGCA TAGAAGTCAA AGCAAAAACA AACCAAAGAA     240
AGGAGCCACA AGAGTAAAAC TGTTCAACAG TTAATAGTTC AAACTAAGCC ATTGAATCTA     300
TCATTGGGAT CGTTAAAATG AATCTTCCTA CACCTTGCAG TGTATGATTT AACTTTTACA     360
GAACACAAGC CAAGTTTAAA ATCAGCAGTA GAGATATTAA AATGAAAAGG TTTGCTAATA     420
GAGTAACATT AAATACCCTG AAGGAAAAAA AACCTAAATA TCAAAATAAC TGATTAAAAT     480
TCACTTGCAA ATTAGCACAC GAATATGCAA CTTGGAAATC ATGCAGTGTT TTATTTAAGA     540
AAACATAAAA CAAAACTATT AAAATAGTTT TAGAGGGGGT AAAATCCAGG TCCTCTGCCA     600
GGATGCTAAA ATTAGACTTC AGGGGAATTT TGAAGTCTTC AATTTTGAAA CCTATTAAAA     660
AGCCCATGAT TACAGTTAAT TAAGAGCAGT GCACGCAACA GTGACACGCC TTTAGAGAGC     720
ATTACTGTGT ATGAACATGT TGGCTGCTAC CAGCCACAGT CAATTTAACA AGGCTGCTCA     780
GTCATGAACT TAATACAGAG AGAGCACGCC TAGGCAGCAA GCACAGCTTG CTGGGCCACT     840
TTCCTCCCTG TCGTGACACA ATCAATCCGT GTACTTGGTG TATCTGAAGC GCACGCTGCA     900
CCGCGGCACT GCCCGGCGGG TTTCTGGGCG GGGAGCGATC CCCGCGTCGC CCCCCGTGAA     960
ACCGACAGAG CCTGGACTTT CAGGAGGTAC AGCGGCGGTC TGAAGGGGAT CTGGGATCTT    1020
GCAGAGGGAA CTTGCATCGA AACTTGGGCA GTTCTCCGAA CCGGAGACTA AGCTTCCCCG    1080
AGCAGCGCAC TTTGGAGACG TGTCCGGTCT ACTCCGGACT CGCATCTCAT TCCACTCGGC    1140
CATAGCCTTG GCTTCCCGGC GACCTCAGCG TGGTCACAGG GGCCCCCCTG TGCCCAGGGA    1200
```

| | |
|---|---|
| A ATG TTT CAA GCT TTT CCC GGA GAC TAC GAC TCC GGC TCC CGG TGT<br>   Met Phe Gln Ala Phe Pro Gly Asp Tyr Asp Ser Gly Ser Arg Cys<br>    1                5                       10               15 | 1246 |
| AGC TCA TCA CCC TCC GCC GAG TCT CAG TAC CTG TCT TCG GTG GAC TCC<br>Ser Ser Ser Pro Ser Ala Glu Ser Gln Tyr Leu Ser Ser Val Asp Ser<br>                  20                    25                  30 | 1294 |
| TTC GGC AGT CCA CCC ACC GCC GCC GCC TCC CAG GAG TGC GCC GGT CTC<br>Phe Gly Ser Pro Pro Thr Ala Ala Ala Ser Gln Glu Cys Ala Gly Leu<br>         35                    40                  45 | 1342 |
| GGG GAA ATG CCC GGC TCC TTC GTG CCA ACG GTC ACC GCA ATC ACA ACC<br>Gly Glu Met Pro Gly Ser Phe Val Pro Thr Val Thr Ala Ile Thr Thr<br>        50                    55                  60 | 1390 |
| AGC CAG GAT CTT CAG TGG CTC GTG CAA CCC ACC CTC ATC TCT TCC ATG<br>Ser Gln Asp Leu Gln Trp Leu Val Gln Pro Thr Leu Ile Ser Ser Met<br>     65                 70                  75 | 1438 |
| GCC CAG TCC CAG GGG CAG CCA CTG GCC TCC CAG CCT CCA GCT GTT GAC<br>Ala Gln Ser Gln Gly Gln Pro Leu Ala Ser Gln Pro Pro Ala Val Asp<br> 80                     85                  90                  95 | 1486 |
| CCT TAT GAC ATG CCA GGA ACC AGC TAC TCA ACC CCA GGC CTG AGT GCC<br>Pro Tyr Asp Met Pro Gly Thr Ser Tyr Ser Thr Pro Gly Leu Ser Ala<br>              100                 105              110 | 1534 |
| TAC AGC ACT GGC GGG GCA AGC GGA AGT GGT GGG CCT TCA ACC AGC ACA<br>Tyr Ser Thr Gly Gly Ala Ser Gly Ser Gly Gly Pro Ser Thr Ser Thr<br>            115                 120              125 | 1582 |
| ACC ACC AGT GGA CCT GTG TCT GCC CGT CCA GCC AGA GCC AGG CCT AGA<br>Thr Thr Ser Gly Pro Val Ser Ala Arg Pro Ala Arg Ala Arg Pro Arg<br>        130                 135                 140 | 1630 |
| AGA CCC CGA GAA GAG ACA CTT ACC CCA GAA GAA GAA GAA AAG CGA AGG<br>Arg Pro Arg Glu Glu Thr Leu Thr Pro Glu Glu Glu Glu Lys Arg Arg<br>145                     150                 155 | 1678 |
| GTT CGC AGA GAG CGG AAC AAG CTG GCT GCA GCT AAG TGC AGG AAC CGT<br>Val Arg Arg Glu Arg Asn Lys Leu Ala Ala Ala Lys Cys Arg Asn Arg<br>160                    165                170              175 | 1726 |
| CGG AGG GAG CTG ACA GAT CGA CTT CAG GCG GAA ACT GAT CAG CTT GAA<br>Arg Arg Glu Leu Thr Asp Arg Leu Gln Ala Glu Thr Asp Gln Leu Glu<br>              180                 185              190 | 1774 |
| GAG GAA AAG GCA GAG CTG GAG TCG GAG ATC GCC GAG CTG CAA AAA GAG<br>Glu Glu Lys Ala Glu Leu Glu Ser Glu Ile Ala Glu Leu Gln Lys Glu<br>            195                   200              205 | 1822 |
| AAG GAA CGC CTG GAG TTT GTC CTG GTG GCC CAC AAA CCG GGC TGC AAG<br>Lys Glu Arg Leu Glu Phe Val Leu Val Ala His Lys Pro Gly Cys Lys<br>         210                   215               220 | 1870 |
| ATC CCC TAC GAA GAG GGG CCG GGG CCA GGC CCG CTG GCC GAG GTG AGA<br>Ile Pro Tyr Glu Glu Gly Pro Gly Pro Gly Pro Leu Ala Glu Val Arg<br>225                     230                 235 | 1918 |
| GAT TTG CCA GGG TCA ACA TCC GCT AAG GAA GAC GGC TTC GGC TGG CTG<br>Asp Leu Pro Gly Ser Thr Ser Ala Lys Glu Asp Gly Phe Gly Trp Leu<br>240                    245                250              255 | 1966 |
| CTG CCG CCC CCT CCA CCA CCC CCC CTG CCC TTC CAG AGC AGC CGA GAC<br>Leu Pro Pro Pro Pro Pro Pro Pro Leu Pro Phe Gln Ser Ser Arg Asp<br>                    260                   265              270 | 2014 |
| GCA CCC CCC AAC CTG ACG GCT TCT CTC TTT ACA CAC AGT GAA GTT CAA<br>Ala Pro Pro Asn Leu Thr Ala Ser Leu Phe Thr His Ser Glu Val Gln<br>              275                   280               285 | 2062 |
| GTC CTC GGC GAC CCC TTC CCC GTT GTT AGC CCT TCG TAC ACT TCC TCG<br>Val Leu Gly Asp Pro Phe Pro Val Val Ser Pro Ser Tyr Thr Ser Ser<br>         290                   295               300 | 2110 |
| TTT GTC CTC ACC TGC CCG GAG GTC TCC GCG TTC GCC GGC GCC CAA CGC<br>Phe Val Leu Thr Cys Pro Glu Val Ser Ala Phe Ala Gly Ala Gln Arg<br>        305                   310               315 | 2158 |

| | | | | | | | | | | | | | | | |
|---|---|---|---|---|---|---|---|---|---|---|---|---|---|---|---|
|ACC|AGC|GGC|AGC|GAG|CAG|CCG|TCC|GAC|CCG|CTG|AAC|TCG|CCC|TCC|CTT|
|Thr|Ser|Gly|Ser|Glu|Gln|Pro|Ser|Asp|Pro|Leu|Asn|Ser|Pro|Ser|Leu|
|320| | | | |325| | | |330| | | | | |335|

2206

CTT GCT CTG T AAACTCTTTA GACAAACAAA ACAAACAAAC CCGCAAGGAA    2256
Leu Ala Leu

```
CAAGGAGGAG GAAGATGAGG AGGAGAGGGG AGGAAGCAGT CCGGGGGTGT GTGTGTGGAC    2316
CCTTTGACTC TTCTGTCTGA CCACCTGCCG CCTCTGCCAT CGGACATGAC GGAAGGACCT    2376
CCTTTGTGTT TTGTGCTCCG TCTCTGGTTT TCTGTGCCCC GGCGAGACCG GAGAGCTGGT    2436
GACTTTGGGG ACAGGGGGTG GGGCGGGGAT GGACACCCCT CCTGCATATC TTTGTCCTGT    2496
TACTTCAACC CAACTTCTGG GGATAGATGG CTGGCTGGGT GGGTAGGGTG GGGTGCAACG    2556
CCCACCTTTG GCGTCTTGCG TGAGGCTGGA GGGGAAAGGG TGCTGAGTGT GGGGTGCAGG    2616
GTGGGTTGAG GTCGAGCTGG CATGCACCTC AGAGAGACC  CAACGAGGAA ATGACAGCAC    2676
CGTCCTGTCC TTCTTTTCCC CCACCCACCC ATCCACCCTC AAGGGTGCAG GGTGACCAAG    2736
ATAGCTCTGT TTTGCTCCCT CGGGCCTTAG CTGATTAACT TAACATTTCC AAGAGGTTAC    2796
AACCTCCTCC TGGACGAATT GAGCCCCCGA CTGAGGGAAG TCGATGCCCC CTTTGGGAGT    2856
CTGCTAACCC CACTTCCCGC TGATTCCAAA ATGTGAACCC CTATCTGACT GCTCAGTCTT    2916
TCCCTCCTGG GAAAACTGGC TCAGGTTGGA TTTTTTTCCT CGTCTGCTAC AGAGCCCCCT    2976
CCCAACTCAG GCCCGCTCCC ACCCCTGTGC AGTATTATGC TATGTCCCTC TCACCCTCAC    3036
CCCCACCCCA GGCGCCCTTG GCCGTCCTCG TTGGGCCTTA CTGGTTTTGG GCAGCAGGGG    3096
GCGCTGCGAC GCCCATCTTG CTGGAGCGCT TTATACTGTG AATGAGTGG  CGGATTGCTG    3156
GGTGCGCCGG ATGGGATTGA CCCCCAGCCC TCCAAAACTT TCCCTGGGCC TCCCCTTCTT    3216
CCACTTGCTT CCTCCCTCCC CTTGACAGGG AGTTAGACTC GAAAGGATGA CCACGACGCA    3276
TCCCGGTGGC CTTCTTGCTC AGGCCCCAGA CTTTTTCTCT TTAAGTCCTT CGCCTTCCCC    3336
AGCCTAGGAC GCCAACTTCT CCCCACCCTG GGAGCCCCGC ATCCTCTCAC AGAGGTCGAG    3396
GCAATTTTCA GAGAAGTTTT CAGGGCTGAG GCTTTGGCTC CCCTATCCTC GATATTTGAA    3456
TCCCCAAATA TTTTTGGACT AGCATACTTA AGAGGGGGCT GAGTTCCCAC TATCCCACTC    3516
CATCCAATTC CTTCAGTCCC AAAGACGAGT TCTGTCCCTT CCCTCCAGCT TTCACCTCGT    3576
GAGAATCCCA CGAGTCAGAT TTCTATTTTT TAATATTGGG GAGATGGGCC CTACCGCCCG    3636
TCCCCCGTGC TGCATGGAAC ATTCCATACC CTGTCCTGGG CCCTAGGTTC CAAACCTAAT    3696
CCCAAACCCC ACCCCAGCT  ATTTATCCCT TTCCTGGTTC CCAAAAAGCA CTTATATCTA    3756
TTATGTATAA ATAAATATAT TATATATGAG TGTGCGTGTG TGTGCGTGTG CGTGCGTGCG    3816
TGCGTGCGTG CGAGCTTCCT TGTTTTCAAG TGTGCTGTGG AGTTCAAAAT CGCTTCTGGG    3876
GATTTGAGTC AGACTTTCTG GCTGTCCCTT TTTGTCACCT TTTTGTTGTT GTCTCGGCTC    3936
CTCTGGCTGT TGGAGACAGT CCCGGCCTCT CCCTTTATCC TTTCTCAAGT CTGTCTCGCT    3996
CAGACCACTT CCAACATGTC TCCACTCTCA ATGACTCTGA TCTCCGGTTG TCTGTTAATT    4056
CTGGATTTGT CGGGGACATG CAATTTTACT TCTGTAAGTA AGTGTGACTG GGTGGTAGAT    4116
TTTTTACAAT CTATATCGTT GAGAATTC                                       4144
```

( 2 ) INFORMATION FOR SEQ ID NO:2:

( i ) SEQUENCE CHARACTERISTICS:
        ( A ) LENGTH: 338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Phe Gln Ala Phe Pro Gly Asp Tyr Asp Ser Gly Ser Arg Cys Ser
 1               5                  10                  15
Ser Ser Pro Ser Ala Glu Ser Gln Tyr Leu Ser Ser Val Asp Ser Phe
            20                  25                  30
Gly Ser Pro Pro Thr Ala Ala Ala Ser Gln Glu Cys Ala Gly Leu Gly
            35                  40                  45
Glu Met Pro Gly Ser Phe Val Pro Thr Val Thr Ala Ile Thr Thr Ser
     50              55                  60
Gln Asp Leu Gln Trp Leu Val Gln Pro Thr Leu Ile Ser Ser Met Ala
 65              70                  75                      80
Gln Ser Gln Gly Gln Pro Leu Ala Ser Gln Pro Pro Ala Val Asp Pro
             85                  90                  95
Tyr Asp Met Pro Gly Thr Ser Tyr Ser Thr Pro Gly Leu Ser Ala Tyr
            100                 105                 110
Ser Thr Gly Gly Ala Ser Gly Ser Gly Gly Pro Ser Thr Ser Thr Thr
        115             120                 125
Thr Ser Gly Pro Val Ser Ala Arg Pro Ala Arg Ala Arg Pro Arg Arg
    130                 135             140
Pro Arg Glu Glu Thr Leu Thr Pro Glu Glu Glu Glu Lys Arg Arg Val
145                 150                 155                 160
Arg Arg Glu Arg Asn Lys Leu Ala Ala Ala Lys Cys Arg Asn Arg Arg
                165                 170                 175
Arg Glu Leu Thr Asp Arg Leu Gln Ala Glu Thr Asp Gln Leu Glu Glu
            180                 185             190
Glu Lys Ala Glu Leu Glu Ser Glu Ile Ala Glu Leu Gln Lys Glu Lys
        195                 200             205
Glu Arg Leu Glu Phe Val Leu Val Ala His Lys Pro Gly Cys Lys Ile
    210                 215             220
Pro Tyr Glu Glu Gly Pro Gly Pro Gly Pro Leu Ala Glu Val Arg Asp
225                 230                 235                 240
Leu Pro Gly Ser Thr Ser Ala Lys Glu Asp Gly Phe Gly Trp Leu Leu
            245                 250                 255
Pro Pro Pro Pro Pro Pro Pro Leu Pro Phe Gln Ser Ser Arg Asp Ala
            260                 265                 270
Pro Pro Asn Leu Thr Ala Ser Leu Phe Thr His Ser Glu Val Gln Val
        275                 280             285
Leu Gly Asp Pro Phe Pro Val Val Ser Pro Ser Tyr Thr Ser Ser Phe
    290                 295             300
Val Leu Thr Cys Pro Glu Val Ser Ala Phe Ala Gly Ala Gln Arg Thr
305                 310             315                 320
Ser Gly Ser Glu Gln Pro Ser Asp Pro Leu Asn Ser Pro Ser Leu Leu
            325                 330                 335
Ala Leu
```

The foregoing is meant to illustrate, but not to limit, the scope of the invention. Indeed, those of ordinary skill in the art can readily envision and produce further embodiments, based on the teachings herein, without undue experimentation.

We claim:

1. An isolated polynucleotide encoding a trans-repressing FosB2 protein, wherein the protein is characterized by:

(a) having a leucine zipper domain; and
(b) forming a heterodimer with a Jun related protein, wherein the heterodimer is capable of:
 (i) binding to an AP-1 site; and
 (ii) suppressing transcriptional transactivation of a promoter containing the AP-1 site; and
(c) having an amino acid sequence of Sequence ID No. 2, wherein amino acids 238–284 are deleted there-from.

2. The polynucleotide of claim 1, wherein the Jun related protein is selected from the group consisting of c-Jun, Jun B and Jun D.

3. A polynucleotide of claim 1, wherein the polynucleotide is DNA.

4. A host cell containing the polynucleotide of claim 1.

5. A recombinant expression vector containing the polynucleotide of claim 1.

6. The vector of claim 5, which is a colloidal dispersion system.

7. The vector of claim 6, wherein the colloidal dispersion system is a liposome.

8. The vector of claim 7, wherein the liposome is essentially target specific.

9. The vector of claim 8, wherein the liposome is anatomically targeted.

10. The vector of claim 8, wherein the liposome is mechanistically targeted.

11. The vector of claim 10, wherein the mechanistic targeting is passive.

12. The vector of claim 10, wherein the mechanistic targeting is active.

13. The vector of claim 12, wherein the liposome is actively targeted by coupling with a moiety selected from the group consisting of a sugar, a glycolipid, and a protein.

14. The vector of claim 13, wherein the protein moiety is an antibody.

15. The vector of claim 5, which is a virus.

16. The vector of claim 15, wherein the virus is an RNA virus.

17. The vector of claim 11, wherein the RNA virus is a retrovirus.

18. The vector of claim 17, wherein the retrovirus is essentially target specific.

19. The vector of claim 18, wherein the moiety for target specificity is selected from the group consisting of a sugar, a glycolipid, and a protein.

20. The vector of claim 19, wherein the protein is an antibody.

* * * * *